United States Patent

Pak Wai

[11] Patent Number: 6,050,939
[45] Date of Patent: Apr. 18, 2000

[54] THROAT MIRROR

[76] Inventor: Martin Pak Wai, 2C, Tower 2, Parc Regal, 19 Ho Man Tin Hill Road, Kowloon, The Hong Kong Special Administrative Region of the People's Republic of China

[21] Appl. No.: 09/324,793

[22] Filed: Jun. 3, 1999

[51] Int. Cl.[7] .................................................. A61B 1/247
[52] U.S. Cl. ............................. 600/248; 600/247; 433/30
[58] Field of Search .................................... 600/184, 188, 600/189, 199, 245, 246, 247, 248; 433/3, 30, 31; 359/872, 875, 876, 877, 882

[56] References Cited

U.S. PATENT DOCUMENTS

| 300,524 | 6/1884 | Starr ..................................... 600/248 X |
| 998,021 | 7/1911 | Marcy .................................. 600/248 X |
| 1,036,000 | 8/1912 | Pease ................................... 600/248 X |
| 2,014,879 | 9/1935 | Brooks ................................. 600/246 X |
| 2,283,560 | 5/1942 | Kretchmer . | |
| 3,003,397 | 10/1961 | Jacobus . | |
| 3,004,474 | 10/1961 | Hund . | |
| 3,870,037 | 3/1975 | Cadariu et al. ........................ 600/189 |
| 4,915,626 | 4/1990 | Lemmey ................................... 433/31 |

*Primary Examiner*—Jeffrey A. Smith
*Attorney, Agent, or Firm*—Jackson Walker L.L.P.

[57] ABSTRACT

A laryngeal mirror arrangement comprises a palm-grippable housing that supports a thin elongate shank. A mirror is pivotably mounted at the end of the shank and controlled to pivot by movement of a finger trigger. A hand torch slidably fits into a cylindrical hollow formed in the housing to focus a beam of light onto the mirror for use in a larynx inspection.

13 Claims, 2 Drawing Sheets

THROAT MIRROR

BACKGROUND OF THE INVENTION

1. Field of the Invention

The invention relates to a throat mirror.

2. Description of Prior Art

A throat mirror in the form of a laryngeal mirror is well-known and used by medical practitioners to view the larynx. The normal mirror arrangement that has been used for many decades comprises a shaft having a fixed angled mirror attached to its remote end. The other end of the shaft is held by the practitioner and moved into position to view the larynx of a patient. The larynx is never-the-less difficult to view satisfactorily and the presence of the mirror in the throat of a patient, especially if the mirror is moved about too much to aid viewing, can easily lead to wretching and vomiting.

It has already been proposed to use fibre optic techniques to provide suitable instruments for larynx inspection. However, fibre optic light sources require considerable electrical power and the overall construction of such instruments leads to significant expense.

SUMMARY OF THE INVENTION

It is an object of the invention to overcome or at least reduce this problem.

According to the invention there is provided a throat mirror arrangement comprising a handle, an elongate shank attached to the handle at one end and having a mirror pivotably mounted at its remote end, including a manually operable lever adjacent the handle for altering the relative angle of the mirror.

The handle preferably comprises a palm grippable housing and the lever is pivotably mounted for operation as a finger trigger.

A removably mounted light source is preferably supported by the handle.

The shank is preferably removably attached to the handle and the mirror may be removably attached to the remote end of the shank.

The mirror may have a reflective surface that is formed or coated with anti-fog material.

The throat mirror arrangement may include a thin rod extending along the shank and a biassed mechanical coupling between the trigger and the rod, in which longitudinal movement of the rod caused by movement of the trigger is arranged to cause the mirror to pivot.

BRIEF DESCRIPTION OF THE DRAWINGS

A laryngeal and nasopharyngeal mirror arrangement according to the invention will now be described by way of example with reference to the accompanying drawing in which.

DESCRIPTION OF THE PREFERRED EMBODIMENT

Figure 1:
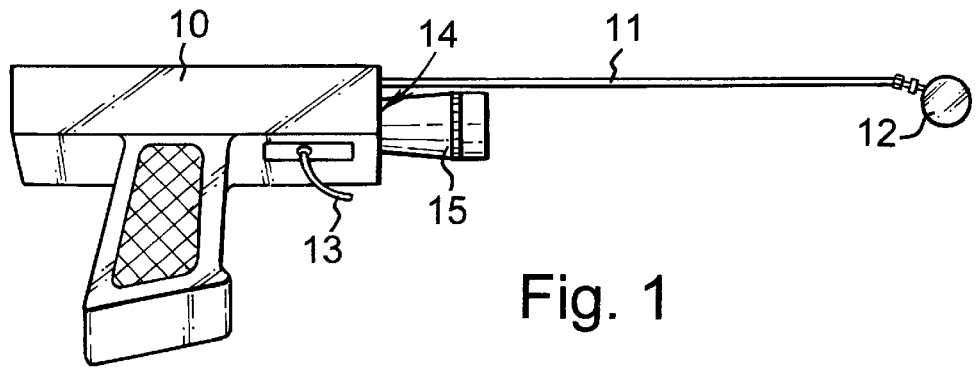
FIG. 1 is a side view of a laryngeal mirror arrangement.

Referring to the drawings, in FIG. 1 a palm-grippable housing 10 supports a thin stainless steel elongate hollow shank 11. A circular mirror 12 is pivotably supported at the remote end of the shank 11. A pivotably mounted finger trigger 13 fits to the housing 10 for operation to cause the mirror 12 to pivot (as described below). The housing has a cylindrical hollow 14, better seen in FIG. 2, into which a hand torch 15 slidably fits for focusing a beam of light on the mirror 12 in use.

Figure 2:
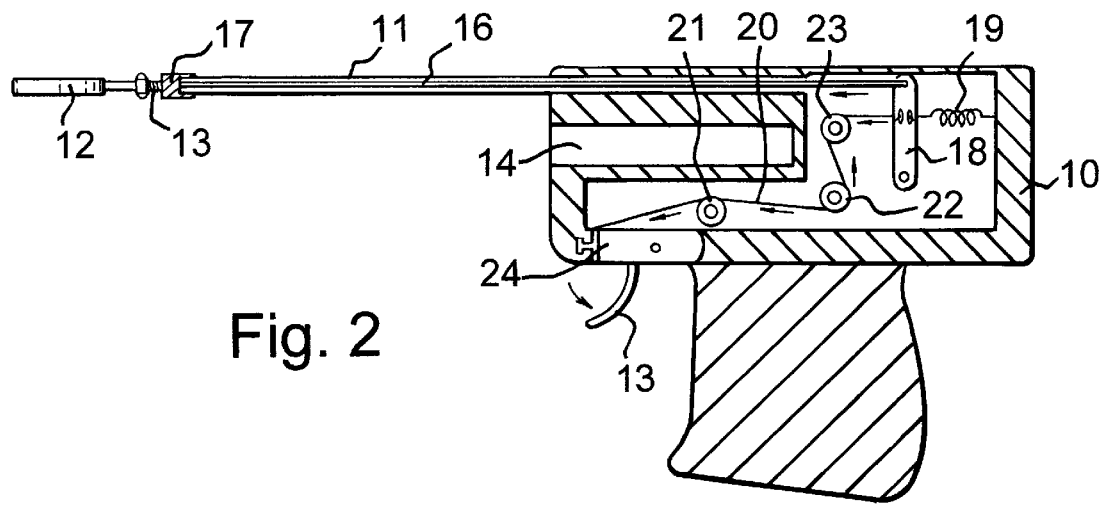
FIG. 2 is a cross-sectional side view of the arrangement of FIG. 1.

In FIG. 2, the torch 15 is not present in the hollow 14 but otherwise the components of FIG. 1 are all shown. A thin stainless steel operating rod 16 extends along inside the shank 11 with its remote end bearing against an arcuate inner surface of a pivotable joint piece 17. Movement of the rod 16 causes the mirror 12 to pivot, as required. The other end of the rod 16 is anchored to a pivotable lever 18 that is spring biassed by a spring 19 and connected to one end of a wire 20 that extends over pulleys 21, 22 and 23 to a slider 24. The slider is moved backwards and forwards by the trigger 13.

In use, the practitioner inserts the mirror into the throat of a patient, to illuminate the larynx or other region of inspection with the torch, and by using the trigger to tilt the mirror, carries out an inspection. Quite small movements of the trigger provide considerable angular adjustments of the mirror, due to the mechanical advantage of the described mechanism. The mirror is returned to a "null" position by the spring 19.

Figure 3:
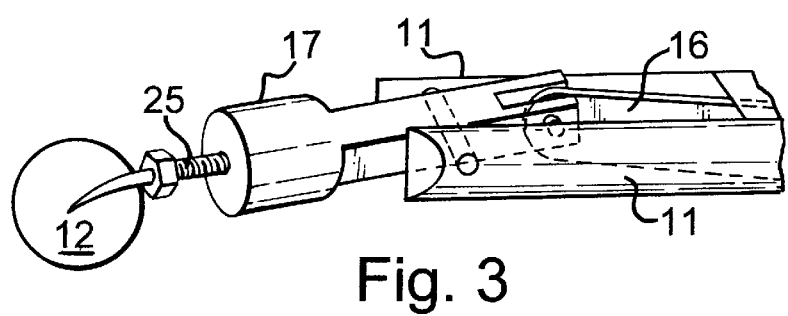
FIG. 3 is an enlarged diagrammatic isometric view of part of the arrangement of FIG. 1.

In FIG. 3, it can be seen that a mirror tilting mechanism comprises the joint piece 17 which is pivotable mounted to the end of the shank 11 and pivotably connected to the end of the rod 16. The mirror is fitted at the end of the shank 11 by a screw fitting 25. This allows other larger or smaller mirrors to be readily fitted where desired.

The reflective surface of the mirror 12 is preferably made or coated with an anti-fog agent, such as COMPACT VISION (trade mark), which remains intact even when the mirror is cleaned or sterilised.

Figure 4:
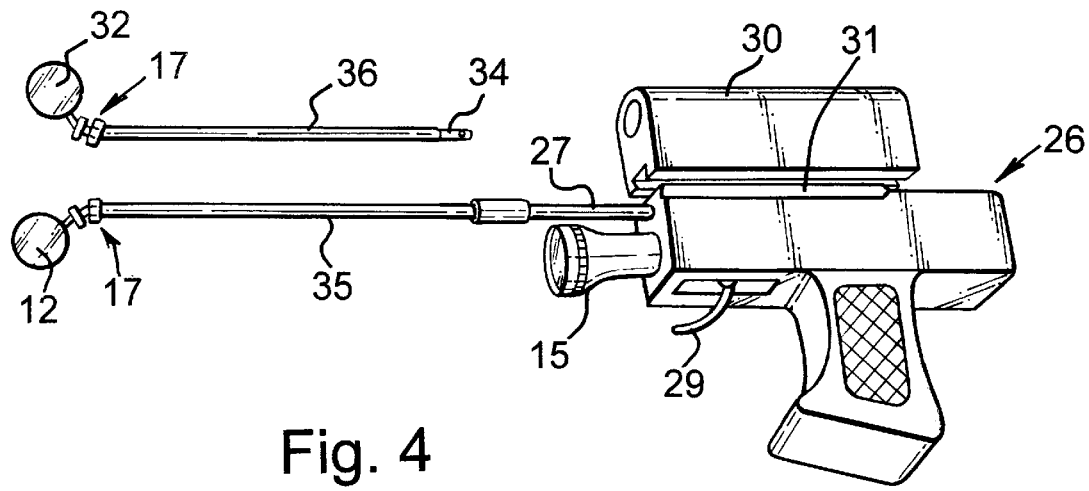
FIG. 4 is an isometric view of another throat mirror arrangement similar to the arrangement of FIG. 1 for larynx and pharynx examinations.
Figure 5:
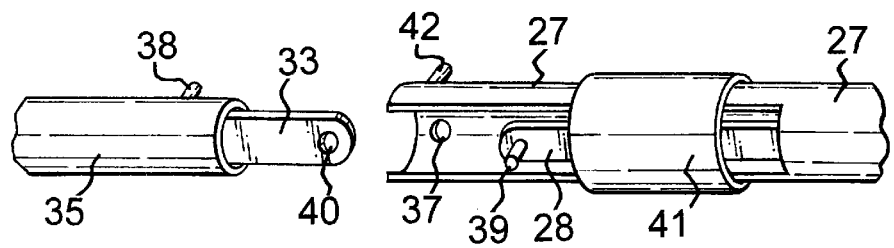
FIG. 5 shows an isometric view of a mechanical connection used in the throat mirror arrangement of FIG. 4.

In FIGS. 4 and 5, a palm gripple housing 26 has a hollow stub 27 inside which an actuator rod 28 can slide. The rod 28 is moved backwards and forwards when a trigger 29 is moved, using a wire and pulleys (not shown) inside the housing in a manner shown in FIG. 2.

The torch 15 is shown positioned in a hollow in the housing 26. A slidable and removable torch holder 30 can fit in use to rails 31 integrally formed in the top of the housing 26. A torch (not shown) fits inside or in a hollow in the holder 30. The torch can be moved independently, or together with the holder 30, to focus a beam of light onto a mirror 32 when fitted to the housing 26 as explained below.

FIG. 4 shows the two mirrors 12 and 32 that are used respectively for examining a patient's larynx and patient's nasopharynx. The mirrors 12 and 32 are pivoted downwards or upwards respectively when respective operating rods 33 and 34 are moved along inside respective hollow shanks 35 and 36 by the actuating rod 28. The mirror tilting mechanism (not shown) for each rod 33 and 34 is the same as shown in FIG. 3. The only difference between the two mirror pivoting support arrangements, when in use, is that for the mirror 12, the remote end of the rod 33 starts from a position above the pivotal axis of the joint piece 17 and moves further upwards, and for the mirror 32 the remote end of the rod 34 starts below that pivotal axis and moves downwards. This means that the mirrors 12 and 32 will be rotated about arcs in opposite directions to one another by pressing on the trigger 29.

In FIG. 5, a releasable connection between the actuating rod 28 and the operating rod 33 is shown. The stub 27 slidingly fits over and around the shank 35 so that an aperture 37 fits onto a pin 38 on the outside of the shank 35. At the same time, a pin 39 is entered through a hole 40 in a near end of the operating rod 33. Once this engagement of the stub 27 to the shank 35 is completed, a sleeve 41 can be slid forwards (to the left in the Figure) and against a stop 42 so that the operating rod 33 cannot thereafter become disengaged from the pin 39. In this way, the shank 35 is in effect readily attached to and removable from the housing 26. This feature greatly facilitates complete sterilisation of the shank 35 and the mirror 12. It will also be noted in this respect that the shanks 35 and 36 are relatively long so that sterilisation is effective along the shanks and far from the mirrors. This ensures that all parts of the throat mirror arrangement that come into contact with the patient in use, for example contacting his tongue and lips, can be readily and efficiently sterilised.

It will be apparent that the mirror 12 and the shank 35, and the mirror 32 and the shank 36 are or can be identical. Thus in order to "convert" a laryngeal mirror into a nasopharynx mirror the shank 35 is merely fitted to the housing 26 in an opposite sense (that is, rotated 180° from the orientation shown in FIG. 5). It will be necessary to provide a second or like stud 38 on the opposite side of the shank 35 for fitting into the aperture 37. In that case, the mirror 12 will tilt upwards in FIG. 4 instead of downwards, when the actuating rod 28 is moved to the left, in the Figure, by pressing on the trigger 29.

Indeed, the described mirror arrangements could be used "upside down" although rather less convenient for the operator. Thus, for example, the laryngeal mirror in FIG. 1 could be used as a nasopharyngeal mirror simply by turning the housing 10 upside down and having the trigger 13 pointing upwards. It is also possible, and sometimes more convenient, to have the trigger mounted in the housing 10 such that the trigger is mounted "at one side". Thus, for example for larynx examination, the housing 10 is held with the trigger 13 at the left of the housing 10 and for pharynx examination the housing 10 is held with the trigger 13 at the right of the housing. In each case, the trigger will be movable through a plane that is generally horizontal during use.

In FIG. 4, it will be appreciated that the embodiment has provision for using two torches, or one torch in one of two locations, for directing light in a path below and above the shanks 35 and 36 respectively. Other configurations for a torch are feasible, in which the torch provides flood light illumination from one location of the housing 10 which may be quite practical and sufficient or satisfactory for both larynx and pharynx examinations.

I claim:

1. A throat mirror arrangement comprising a handle, an elongate shank attached to the handle at one end and having a mirror pivotably mounted at its remote end, including a manually operable lever adjacent the handle for altering the relative angle of the mirror, and a removably mounted light source supported by the handle.

2. A mirror arrangement according to claim 1, in which the handle comprises a palm grippable housing and the lever is pivotably mounted for operation as a finger trigger.

3. A mirror arrangement according to claim 1, in which the shank is removably attached to the handle.

4. A mirror arrangement according to claim 3, in which the shank is arranged to be attached in two optional opposite orientations so that the mirror can be used for larynx and pharynx, examinations accordingly.

5. A mirror arrangement according to claim 1, in which the mirror is removably attached to a remote end of the shank.

6. A mirror arrangement according to claim 1, in which the mirror has a reflective surface that is formed or coated with anti-fog material.

7. A mirror arrangement according to claim 1, including a thin rod extending along the shank and a biassed mechanical coupling between the trigger and the rod, in which longitudinal movement of the rod caused by movement of the trigger is arranged to cause the mirror to pivot.

8. A throat mirror arrangement comprising a handle, an elongate shank removably attached to the handle at one end and having a mirror pivotably mounted at its remote end, including a manually operable lever adjacent the handle for altering the relative angle of the mirror, in which the shank is arranged to be attached in two optional opposite orientations so that the mirror can be used for larynx and pharynx examinations accordingly.

9. A mirror arrangement according to claim 8, in which the handle comprises a palm grippable housing and the lever is pivotably mounted for operation as a finger trigger.

10. A mirror arrangement according to claim 8, including a removably mounted light source supported by the handle.

11. A mirror arrangement according to claim 8, in which the mirror is removably attached to a remote end of the shank.

12. A mirror arrangement according to claim 8, in which the mirror has a reflective surface that is formed or coated with anti-fog material.

13. A mirror arrangement according to claim 8, including a thin rod extending along the shank and a biased mechanical coupling between the trigger and the rod, in which longitudinal movement of the rod caused by movement of the trigger is arranged to cause the mirror to pivot.

* * * * *